United States Patent
Tropsch et al.

(10) Patent No.: US 6,214,885 B1
(45) Date of Patent: Apr. 10, 2001

(54) USE OF POLYMERS CONTAINING β-HYDROXYALKYLVINYLAMINE UNITS AS BIOCIDES

(75) Inventors: Jürgen Tropsch, Römerberg; Dieter Zeller, Wiesloch; Anton Negele, Deidesheim; Norbert Mahr, Limburgerhof; Jürgen Decker, Trier, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/508,058
(22) PCT Filed: Sep. 5, 1998
(86) PCT No.: PCT/EP98/05623
   § 371 Date: Mar. 7, 2000
   § 102(e) Date: Mar. 7, 2000
(87) PCT Pub. No.: WO99/12418
   PCT Pub. Date: Mar. 18, 1999

(30) Foreign Application Priority Data

Sep. 8, 1997 (DE) ............................. 197 39 355

(51) Int. Cl.$^7$ .................................. A01N 33/08
(52) U.S. Cl. .................. 514/650; 514/653; 514/669; 424/78.08; 424/78.37
(58) Field of Search ............... 424/78.08, 78.37; 514/650, 653, 669

(56) References Cited

U.S. PATENT DOCUMENTS

| | | |
|---|---|---|
| 3,597,314 | 8/1971 | Laube . |
| 3,714,259 | 1/1973 | Lichtenwalter . |
| 4,005,193 | 1/1977 | Green et al. ............ 424/168 |
| 4,255,548 | 3/1981 | Wingard . |
| 4,421,602 | 12/1983 | Brunnmueller . |
| 4,578,515 | 3/1986 | Dawson . |
| 4,778,725 | 10/1988 | Serizawa . |
| 5,246,984 | 9/1993 | Darwen . |
| 5,324,787 | 6/1994 | Pinschmidt . |
| 5,350,784 | 9/1994 | Darwen . |

FOREIGN PATENT DOCUMENTS

| | | |
|---|---|---|
| 25 30 243 | 1/1977 | (DE) . |
| 331 528 | 9/1989 | (EP) . |
| 1071630 | 2/1984 | (SU) . |
| 92/20226 | 11/1992 | (WO) . |
| 97/42229 | 11/1997 | (WO) . |

OTHER PUBLICATIONS

Soc.Poly.Sci.,JP, vol. XXVI, No. 288, 1969,Ikemura.
Derwent, XP 002091790 Abstr. (1980).
J.Poly.Sci,Chem, vol. 31, 335–343 (1993) Kanazawa.
J.Poly.Sci.Chem.vol. 31, 1441–1447 (1993) Kanazawa.
J.Poly.Sci., Chem. vol. 31, 1467–1472 (1993) Kanazawa.
J.Poly.Sci.,Chem. vol. 31, 2873–2876 (1993).
Arch.Pharm. 321, 89–92 (1988) Messinger et al.
Jan. 1987, Heft 1–ISSN 0044–2402, 1–9, Hartmann et al.

*Primary Examiner*—Samuel Barts
*Assistant Examiner*—Brian J. Davis
(74) *Attorney, Agent, or Firm*—Keil & Weinkauf

(57) ABSTRACT

The use of polymers containing β-hydroxyalkylvinylamine units, as obtainable by reacting polymers containing vinylamine units with epoxides of the formula

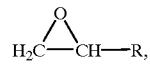

in which R is $C_2$–$C_{28}$ alkyl, phenyl, $C_1$–$C_{18}$ alkylphenyl or $C_2$–$C_{18}$ alkenyl, as biocides.

4 Claims, No Drawings

USE OF POLYMERS CONTAINING β-HYDROXYALKYLVINYLAMINE UNITS AS BIOCIDES

TITLE OF THE INVENTION

This invention is a 371 of PCT EP 98/05,623 filed Sep. 5, 1998.

BACKGROUND OF THE INVENTION

1. Field of the Invention

The invention relates to the use of polymers containing β-hydroxyalkylvinylamine units, as obtainable by reacting polymers containing vinylamine units with epoxides, as biocides.

2. Description of Related Art

Polymers containing vinylamine units are prepared, as is known, by polymerizing acyclic N-vinylcarboxamides, preferably N-vinylformamide, and then hydrolyzing the polymers using acids or bases; cf. U.S. Pat. Nos. 4,421,602, 3,597,314, 4,578,515 and 4,255,548.

The preparation of modified polyvinylamines is also known from the literature. For example, the water-solubility of polyvinylamines is improved by grafting ethylene oxide or propylene oxide onto polyvinylamine; cf. Ikemura, Kobunshi Kagaku, 26 (288), 306–310 (1969).

U.S. Pat. No. 5,324,787 discloses modified polyvinylamines obtainable by reacting at least 0.1 mol % of the amine units of polyvinylamine with a glycidyl ether compound. The reaction produces hydrophobicized polyvinylamines which are used as retention agents in papermaking.

The reaction of polyalkylenepolyamines and monoepoxides or polyepoxides for preparing water-dispersible reactive resins which contain epoxide groups and are used in coating materials is known from U.S. Pat. Nos. 5,246,984 and 5,350,784.

Z. Chem. 27 (1987) 1 discloses specially functionalized polyvinyl alcohols, polyacrylates and polyethylenimines for immobilizing antimicrobially active substances. In the course of the use of such systems, the active substances are released in a controlled manner. According to the information in the publication, however, the antimicrobial activity is based on the release of the biocidal active substances.

SU-A-1,071,630 discloses that copolymers of diallyldimethyl-ammonium chloride and sodium acrylate have a bactericidal activity. EP-A 0 331 528 discloses copolymers of ethylene and dialkylaminoalkylacrylamides having biocidal activity. Antimicrobially active polymers containing vinylphosphonium and vinylsulfonium groups were reported in J. Polym. Sci. part A: Polym. Chem., Vol. 31, 335, 1441, 1467 and 2873 and also in Arch. Pharm. (Weinheim) 321 (1988) 89. Biocidally active polymers containing vinylamine units are known from Makromol. Chemie.

U.S. Pat. No. 4,005,193 describes N-containing polymers as biocides. However, the nitrogen atoms are situated in the main chain of the polymer. Similar polymer structures are also described in U.S. Pat. No. 3,714,259.

BRIEF DESCRIPTION OF THE INVENTION

It is an object of the present invention to provide novel biocidal compositions.

We have found that this object is achieved in accordance with the invention by the use of polymers containing β-hydroxyalkyl-vinylamine units, as obtainable by reacting polymers containing vinylamine units with epoxides of the formula

in which R is $C_2$–$C_{28}$ alkyl, phenyl, $C_1$–$C_{18}$ alkylphenyl or $C_2$–$C_{18}$ alkenyl.

DETAILED DESCRIPTION OF THE INVENTION

The polymers to be used in accordance with the invention, and a process for preparing them, are described in the earlier application P 1 96 17983.1.

Polymers containing vinylamine units are known; cf., for example, U.S. Pat. No. 4,217,214, EP-A-0 071 050 and EP-A-0 216 387. These polymers are obtainable by copolymerizing open-chain N-vinylcarboxamides, alone or together with other monoethylenically unsaturated monomers, and then eliminating the formyl or alkylcarbonyl group from the copolymerized open-chain N-vinylcarboxamide units using acids, bases or enzymes, with the formation of vinylamine units.

The polymers containing vinylamine units are prepared starting, for example, from open-chain N-vinylcarboxamides of the formula

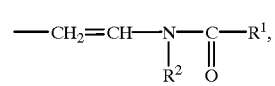

in which $R^1$ and $R^2$ can be identical or different and are hydrogen or $C_1$–$C_6$ alkyl. Examples of suitable monomers are N-vinylformamide ($R^1$=$R^2$=H in formula I), N-vinyl-N-methylformamide, N-vinylacetamide, N-vinyl-N-methylacetamide, N-vinyl-N-ethylacetamide, N-vinyl-N-methylpropionamide and N-vinylpropionamide. To prepare the polymers, the abovementioned monomers can be polymerized either alone, in a mixture with one another, or together with other monoethylenically unsaturated monomers. It is preferred to start from polymers of N-vinylformamide.

Suitable monoethylenically unsaturated monomers are all compounds which can be copolymerized with the open-chain vinylcarboxamides. Examples thereof are vinyl esters of saturated carboxylic acids of 1 to 6 carbon atoms, such as vinyl formate, vinyl acetate, vinyl propionate and vinyl butyrate. Further suitable comonomers are ethylenically unsaturated $C_3$–$C_6$ carboxylic acids, examples being acrylic acid, methacrylic acid, maleic acid, crotonic acid, itaconic acid and vinylacetic acid and also their alkali metal and alkaline earth metal salts, esters, amides and nitriles, examples being methyl acrylate, methyl methacrylate, ethyl acrylate and ethyl methacrylate. Further suitable carboxylic esters are derived from glycols or polyalkylene glycols, with only one OH group being esterified in each case; examples are hydroxyethyl acrylate, hydroxyethyl methacrylate, hydroxypropyl acrylate, hydroxybutyl acrylate, hydroxypropyl methacrylate, hydroxybutyl methacrylate and also acrylic monoesters of polyalkylene glycols having a molecular mass of from 500 to 10,000. Further suitable comonomers are esters of ethylenically unsaturated carboxylic acids with amino alcohols, such as, for example, dimethylaminoethyl acrylate, dimethylaminoethyl methacrylate, diethylaminoethyl acrylate, diethylaminomethyl methacrylate, dimethylaminopropyl acrylate, dimethylaminopropyl methacrylate, diethylaminopropyl acrylate, dimethylaminobutyl acrylate and diethylaminobutyl acrylate. The basic acrylates can be used in the form of the free bases, the salts with mineral acids such as hydrochloric acid, sulfuric acid or nitric acid, the salts with organic acids such as formic acid, acetic acid, propionic acid or sulfonic acid, or in quaternized form. Examples of suitable quaternizing agents are dimethyl sulfate, diethyl sulfate, methyl chloride, ethyl chloride and benzyl chloride. Further suitable comonomers are amides of ethylenically unsaturated carboxylic acids, such as acrylamide, methacrylamide and also N-alkylmonoamides and -diamides of monoethylenically unsaturated carboxylic acids having alkyl radicals of 1 to 6 carbon atoms, examples being N-methylacrylamide, N,N-dimethylacrylamide, N-methylmethacrylamide, N-ethylacrylamide, N-propylacrylamide and tert-butylacrylamide, and also basic (meth)acrylamides, such as dimethylaminoethylacrylamide, dimethylaminoethylmethacrylamide, diethylaminoethylacrylamide, diethylaminoethylmethacrylamide, dimethylaminopropylacrylamide, diethylaminopropylacrylamide, dimethylaminopropylmethacrylamide and diethylaminopropylmethacrylamide, for example.

Further suitable comonomers are N-vinylpyrrolidone, N-vinylcaprolactam, acrylonitrile, methacrylonitrile, N-vinylimidazole and also substituted N-vinylimidazoles such as, for example, N-vinyl-2-methylimidazole, N-vinyl-4-methylimidazole, N-vinyl-5-methylimidazole, N-vinyl-2-ethylimidazole and N-vinylimidazolines such as vinylimidazoline, N-vinyl-2-methylimidazoline and N-vinyl-2-ethylimidazoline, for example. In addition to the free base form, N-vinylimidazoles and N-vinylimidazolines are also used neutralized with mineral acids or organic acids or in quaternized form, quaternization being performed preferably with dimethyl sulfate, diethyl sulfate, methyl chloride or benzyl chloride.

Further suitable comonomers are monomers containing sulfo groups, such as vinylsulfonic acid, allylsulfonic acid, methallylsulfonic acid, styrenesulfonic acid, the alkali metal or ammonium salts of these acids, or 3-sulfopropyl acrylate, for example.

The copolymers also include terpolymers and those polymers which in addition contain at least one further monomer in copolymerized form.

In order to prepare copolymers containing vinylamine units, it is preferred to start from homopolymers of N-vinylformamide or from copolymers containing in copolymerized form
    N-vinylformamide and
    vinyl formate, vinyl acetate, vinyl propionate, acrylonitrile or N-vinylpyrrolidone.

The polymers described above are converted into polymers containing vinylamine units by the action of acids, bases or enzymes. The products, formed by elimination of the group

 (II)

with formation of units of the formula

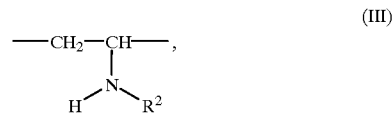 (III)

where $R^2$ is as defined for formula (I), from the copolymerized monomers of the above formula I, are polymers containing vinylamine units.

The copolymers contain for example
    from 99 to 1 mol % of N-vinylcarboxamides of the formula I and
    from 1 to 99 mol % of other monoethylenically unsaturated monomers copolymerizable therewith.

The degree of hydrolysis of the homopolymers of the N-vinylcarboxamides of the formula I and their copolymers can be from 0.1 to 100 mol %, preferably from 10 to 100 mol %. In the majority of cases the degree of hydrolysis of the homopolymers and copolymers is from 50 to 90 mol %. The degree of hydrolysis of the polymers is synonymous with the vinylamine unit content of the polymers. In the case of copolymers containing vinyl esters in copolymerized form, the hydrolysis of the N-vinylformamide units may be accompanied by hydrolysis of the ester groups, forming vinyl alcohol units. This is particularly the case when the copolymers are hydrolyzed in the presence of sodium hydroxide solution. Copolymerized acrylonitrile is likewise chemically modified in the course of hydrolysis. In this case, amide groups or carboxyl groups are formed, for example.

The polymers to be used in accordance with the invention are prepared by reacting polymers containing vinylamine units with epoxides of the formula

 (IV)

in which R is $C_2$–$C_{28}$ alkyl, phenyl, $C_1$–$C_{18}$ alkylphenyl or $C_2$–$C_{18}$ alkenyl.

The epoxides indicated above are known. If the substituent R in the formula indicated for the epoxides is an alkyl group, then it can be a straight-chain, branched or cyclic alkyl group. If the substituent R is an alkenyl, it embraces both straight-chain and branched alkenyl groups. It is preferred to use epoxides of the above formula containing 12 to 20 carbon atoms.

The abovementioned epoxides are reacted with polymers containing vinylamine units at temperatures above 70° C. The reaction is preferably carried out in a solvent. Examples of suitable solvents are $C_1$–$C_4$ alcohols, tetrahydrofuran, dioxane, dimethylformamide and water. The reaction is preferably conducted in aqueous solution. During the reaction the temperatures are, for example, from 70 to 180° C. and are preferably within the range from 75 to 100° C. The reaction is preferably carried out in aqueous solution at a pH of more than 7; for example, in the range from 8 to 13, in particular from 9 to 11. The concentration of the reactants in the aqueous solution or in another suitable solvent is from 1 to 60% by weight, preferably from 10 to 40% by weight. Within the temperature range from 80 to 95° C., the reaction is at an end after from 30 to 180 minutes, for example. When performed at temperatures above 100° C., the reaction in aqueous solution is carried out in apparatus having a pressuretight seal.

The reaction products are modified polyvinylamines containing β-hydroxyalkylvinylamine units of the structure

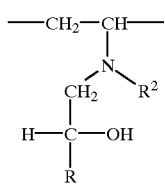

(V)

in which
R is $C_2$–$C_{28}$ alkyl, phenyl, $C_1$–$C_{18}$ alkylphenyl or $C_2$–$C_{18}$ alkenyl and
$R^2$ is H or $C_1$–$C_6$-alkyl.

At least 0.1 mol % of the NH groups of the polymers containing vinylamine units have undergone reaction with epoxides of the formula IV, so that the polymers to be used in accordance with the invention contain at least 0.1 mol % of units of the formula V. To prepare the polymers to be used in accordance with the invention, it is usual to react at least 10 mol % of the NH groups of the polymers containing vinylamine units with epoxides of the formula IV. It is preferred to react from 50 to 90 mol % of the NH groups of the polymers containing vinylamine units with epoxides of the formula IV. Among the epoxides of the formula IV, preference is given to those containing 12 to 20 carbon atoms in the molecule.

If polyvinylamines prepared by hydrolyzing polymers containing N-vinylformamide units are used in the reaction with the epoxides of the formula IV, vinylamine units having a primary amino group are obtained. In the reaction with epoxides of the formula IV, such compounds are able to substitute both hydrogen atoms of the primary amino group. In that case, polymers with units of the formula

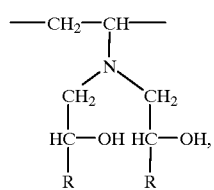

(VI)

are obtained in which
R is $C_2$–$C_{28}$ alkyl, phenyl, $C_1$–$C_{18}$ alkylphenyl or $C_2$–$C_{18}$ alkenyl.

In the formulae V and VI, R is preferably $C_{10}$–$C_{16}$ alkyl.

The modified polyvinylamines contain units of the formula VI in amounts, for example, of up to about 50 mol %, preferably from 5 to 25 mol %.

If partially hydrolyzed N-vinylcarboxamides are used in the reaction with the epoxides of the formula IV, the polymers obtained contain not only units of the structure V and, if appropriate, of the structure VI but also units of nonhydrolyzed vinylcarboxamides. If, for example, copolymers of N-vinylformamide and vinyl formate, vinyl acetate or vinyl propionate are used, then depending on the hydrolysis conditions the products are copolymers containing vinyl formate, vinyl acetate and vinyl propionate units and also the corresponding hydrolysis products of these units, namely vinyl alcohol units. Particular preference is given to polymers containing amine units and units of the formula V,
vinylamine units, N-vinylformamide units and units of the formula V,
vinylamine units, vinyl alcohol units and units of the formula V or
vinylamine units, vinyl propionate units and, if appropriate, vinyl alcohol units and units of the formula V.

The amount of units of the formula V in the polymers to be used in accordance with the invention is at least 0.1 mol % and is usually within the range from 30 to 100 mol %, preferably from 50 to 95 mol %. The polymers to be used in accordance with the invention have molecular masses $M_w$ (determined by the method of light scattering) of from 500 to 50 million, preferably from 10,000 to 2 million. The novel polymers have K values of from 10 to 300, preferably from 30 to 200. The K values are determined in accordance with H. Fikentscher in 5% strength aqueous sodium chloride solution at a pH of 7, a temperature of 25° C. and a polymer concentration of 0.5% by weight; cf. Cellulose-Chemie 13 (1932) 58–64 and 71–74.

The polymers obtainable by the process described above have a strong microbicidal action and can therefore be used to control unwanted microorganisms. The active substances and the formulations preparable therefrom are intended chemically to destroy, deter, render harmless or prevent damage by harmful organisms or to control them in some other way.

The polymers to be used in accordance with the invention and the formulations thereof prevent the microbial infestation of industrial materials and so can be used for in-can preservation. They are also used for the biocidal finishing of products: that is, they can be used for film preservation.

By industrial materials are meant nonliving materials as obtained in industrial processes. Examples of industrial materials to be protected by the use according to the invention of the polymers and formulations against microbial alteration or destruction are as follows:

finishes, drilling oils, dispersions, adhesives, glues, pigment formulations, paper, textiles, textile assistants, leather, leather assistants, wood, coatings, antifouling paints, plastics articles, cosmetics, detergents, cleaning products, cooling lubricants, hydraulic fluids, joint-sealing compounds, putties, thickener solutions and other materials which may be infested or broken down by microorganisms.

The polymers and formulations can also be used in water treatment. By water treatment is meant the addition of the polymers and formulations to process water: for example, for slime control in the paper industry or for the control of harmful organisms in the sugar industry. They prevent or control the growth of microorganisms in cooling circuits, air humidifiers, or in drilling and conveying fluids in the petroleum industry.

The polymers and their formulations can also be used for disinfection.

Examples that may be mentioned of microorganisms which can bring about the breakdown of or a change in industrial materials are bacteria, viruses, spores, yeasts, fungi, algae and slime organisms. The polymers to be used in accordance with the invention and their formulations are preferably active against bacteria, yeasts and fungi.

The following microorganisms may be mentioned by way of example:

*Staphylococcus aureus*
*Escherichia coli*
*Proteus mirabilis*
*Citrobacter freudii*
*Pseudomonas aeruginosa*
*Candida albicans*
*Saccharomyces cerevisiae*
*Alternaria alternate*
*Aspergillus niger*
*Penicillium funiculosum*

Depending on their chemical and physical properties, the polymers to be used in accordance with the invention can be converted into customary formulations and preparations, such as emulsions, suspensions, dispersions, solutions, powders and pastes, for example, or in combination with carrier materials. For this purpose, surface-active substances (e.g., anionic surfactants such as alkylsulfonates, ether sulfates; nonionic surfactants such as fatty alcohol ethoxylates, fatty alcohol es ter ethoxylates, sorbitan esters, polyalkylene glycols; amphoteric surfactants), complexing agents (e.g., ethylenediaminetetraacetic acid, nitrilotriacetic acid, methyiglycinediacetic acid), solubilizers (e.g., alcohols such as ethanol, n-propanol, isopropanol, or glycols, such as propylene glycol and polypropylene glycol), acids or bases (e.g., phosphoric acid, sodium hydroxide solution), inorganic salts and/or further additives (such as corrosion inhibitors, foam suppressants, guide substances, dyes) are added to the formulations and preparations if desired.

Processes for preparing such biocidally active formulations are known to the skilled worker and are described in the relevant literature.

The activity a nd the spectrum of action of the polymers to be used in accordance with the invention and, respectively, of the compositions or formulations preparable therefrom can be raised by adding, if desired, further microbicidally active compounds such as fungicides, bactericides and/or herbicides, insecticides and/or other active substances for the purpose of broadening the spectrum of action or for obtaining particular effects. In many cases, synergistic effects are obtained in this case: that is, the spectrum of action of the mixture exceeds the action of the individual components. Such substances are known per se to the skilled worker and are described in the literature.

Particularly preferred co-components are 5-aminoisothiazoles of the formula VII

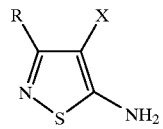

VII in which
R is hydrogen or $C_1$–$C_4$ alkyl and
X is halogen, $NO_2$, CN or SCN
and their metal complexes and acid addition salts.

Preferred compounds are those in which R is $C_1$–$C_4$ alkyl, especially methyl.

Further preferred compounds are those in which X is CN and especially SCN.

In a particularly preferred embodiment use is made of 3-methyl-4-thiocyanato-5-aminoisothiazole (formula VIIc),

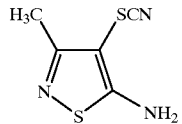

VIIc and its metal complexes and acid addition salts.

The abovementioned aminoisothiazoles VII are obtained using a reaction sequence which is known per se from EP-A-640 597 and in which isothiazoles of the formula VIII,

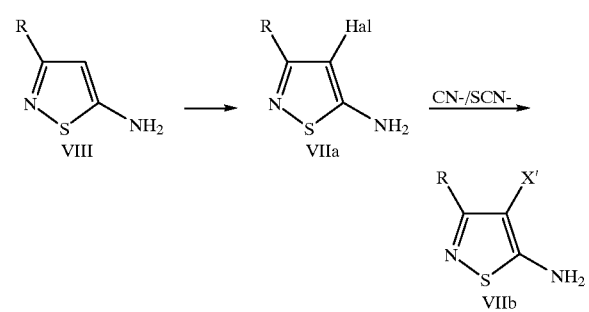

are converted using a halogenating agent into the halogen compounds VIIa, in which Hal is F, Cl, Br or I, which if required are then transformed by reaction with thiocyanates or cyanides into the compounds VIIb, where X' is SCN or CN. The preparation of isothiazoles of the formula VIII is described, for example, in DE-A 17 70 819. The preparation of 3-methyl-5-aminoisothiazole was described by A. Adams et al. in J. Chem. Soc. 1959, 3061.

The microbicidal compositions or concentrates used to protect industrial materials contain the polymers to be used in accordance with the invention, or the active-substance combinations, in a concentration of from 0.005 to 70% by weight, in particular from 0.05 to 40% by weight, based on the overall weight.

The concentrations in which the polymers to be used are employed is guided by the nature and the incidence of the microorganisms to be controlled and by the composition of the material to be protected.

Microbicidal and microbistatic properties are determined experimentally. Highly suitable test methods have been described in detail by the German Society of Hygiene and Microbiology (DGHM) for the testing of disinfectants.

The results in the Use Examples below were determined as follows:

Tube dilution tests were carried out to determine the minimum inhibitory concentration MIC in accordance with the "Guidelines for the Testing and Evaluation of Chemical Disinfection Procedures (status 1.1.81, procedure slightly modified)" using casein peptone-soybean flour peptone medium. Dilution was made with water of standardized hardness without further auxiliaries such as, for example, surfactants. The adjustment of the pH to 7.2±0.2 was carried out with 0.1 mol/l NaOH or 0.1 mol/l HCl. The gradation of the test concentrations was in accordance with the concentration stages proposed by the DGHM. Evaluation was made after incubation at 36° C. for 72 hours.

The table below indicates the strain numbers of the microorganisms:

Test microorganisms:

*Staphylococcus aureus* ATTC 6538
*Escherichia coli* ATTC 11229
*Proteus mirabilis* ATTC 14153
*Pseudomonas aeruginosa* ATTC 15442
*Candida albicans* ATTC 10231

EXAMPLE

A stirred reactor equipped with cooler, thermometer and feed apparatus and with a capacity of 1 liter was charged with an aqueous solution containing 150 g of a fully hydrolyzed polymer comprising 70% N-vinylformamide and 30% vinyl acetate with 70 mol % vinylamine units and 30 mol % vinyl alcohol units and a K value of 90, at a pH from 11 to 13, and 67 g of an epoxide of the formula IV (R=$C_8$ alkyl) were added over the course of 10 minutes at room temperature. The reaction mixture was then heated to 90° C. and stirred at this temperature for 2 hours. The reaction was then at an end. The reaction mixture was cooled and the water used as solvent was removed under reduced pressure. The reaction product was characterized in terms of the β-hydroxyalkylvinylamine unit content by determining the amine number and OH number in accordance with known methods (content 34.7 mol %). The K value of the resulting product was 96.8.

The table below indicates the minimum effective concentration (MIC), the concentrations being based on the respective polymer content.

TABLE 1

| Test microorganism | Polymer from Ex. 1 |
|---|---|
| *Staphylococcus aureus* | 600 |
| *Escherichia coli* | 1600 |
| *Proteus mirabilis* | 6000 |
| *Pseudomonas aeruginosa* | 2000 |
| *Candida albicans* | 1600 |

The results show the good microbicidal action of the polymers to be used in accordance with the invention.

We claim:

1. A method of controlling microorganisms comprising treating said microorganisms with a biocidally effective amount of a biocide containing 6-hydroxyalkylvinylamine units obtained by reacting polymers containing vinylamine units with epoxides of the formula

in which R is $C_2$–$C_{28}$alkyl, phenyl, $C_1$–$C_{18}$alkylphenyl or $C_2$–$C_{18}$alkenyl.

2. The method of claim 1 wherein the biocide is one in which at least 0.1 mol % of the NH groups of the polymers containing vinylamine units has been reacted with epoxides.

3. The method of claim 1 wherein the biocide is one in which at least 10 mol % of the NH groups of the polymers containing vinylamine units has been reacted with epoxides.

4. The method of claim 1 wherein the biocide is one in which at least from 50 to 95 mol % of the NH groups of the polymers containing vinylamine units has been reacted with epoxides.

* * * * *